United States Patent [19]
Buizer et al.

[11] Patent Number: 5,948,909
[45] Date of Patent: Sep. 7, 1999

[54] PROCESS FOR THE STEREOSELECTIVE PREPARATION OF A HETERO-BICYCLIC ALCOHOL ENANTIOMER

[75] Inventors: Nicolaas Buizer; Chris G. Kruse; Klara M. Schenk; Belal Shadid, all of Weesp, Netherlands

[73] Assignee: Duphar International Research B.V., Weesp, Netherlands

[21] Appl. No.: 08/786,306

[22] Filed: Jan. 22, 1997

[30] Foreign Application Priority Data

Jan. 25, 1996 [EP] European Pat. Off. .............. 96200169

[51] Int. Cl.$^6$ ...................... C07D 265/36; C07D 319/14; C07D 317/44
[52] U.S. Cl. ........................... 544/105; 549/366; 549/439
[58] Field of Search ........................... 544/105; 549/366, 549/439

[56] References Cited

FOREIGN PATENT DOCUMENTS 605033  6/1994  European Pat. Off. .
1137035 9/1962  Germany .

OTHER PUBLICATIONS

Tetrahedron Letters, vol. 29, No. 30, 1988, pp. 3671–3674, Short A. Enantioselective Synthesis of (R)–and (S)–2–Hydroxymethyl–1, 4–Benzodioxane, pp. 3671–3672.

Journal of Medicinal Chemistry, vol. 20, No. 7, 1977, Wendel L. Nelson et al: Absolute Configuration of Glycerol Derivatives, pp. 880–884.

Olcott, Chemistry and Industry, "Monoacetates of Hydroquinone and Catechol" vol. 58 pp. 392–393, 1936.

Chemical Abstracts vol. 100, No. 139,086, Schlager, "Ring Substituted Pyrogallol Derivatives" 1983.

*Primary Examiner*—John Kight
*Assistant Examiner*—Raymond Covington
*Attorney, Agent, or Firm*—Stevens, Davis, Miller & Mosher, L.L.P.

[57] ABSTRACT

The invention relates to a method for the stereoselective preparation of a hetero-bicyclic alcohol enantiomer, characterized in that a substantially pure enantiomer of the general formula

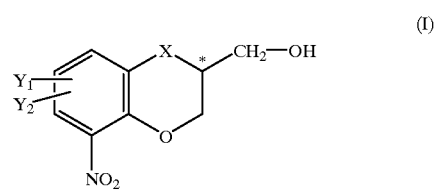

(I)

is prepared from a compound of the general formula

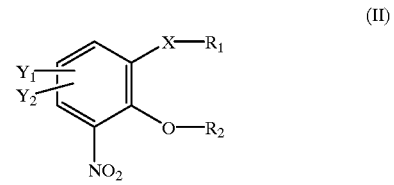

(II)

wherein the variable are as defined as in claim 1. The method comprises the following successive reaction steps:
(i) reaction with a substantially enantiomerically pure compound of the general formula

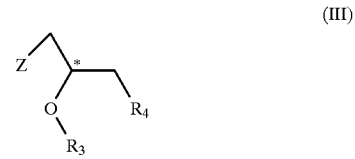

(III)

wherein Z, $R_3$ and $R_4$ are defined as in claim 1;
(ii) subjection of the compound formed to a deprotection/ring-closure reaction;
(iii) optionally deprotection of the hydroxy group of the ring-closed product.

The invention further relates to enantiomerically pure intermediates, the preparation of these intermediates and the preparation of a starting compound.

14 Claims, No Drawings

PROCESS FOR THE STEREOSELECTIVE PREPARATION OF A HETERO-BICYCLIC ALCOHOL ENANTIOMER

The present invention relates to a process for the stereoselective preparation of a hetero-bicyclic alcohol enantiomer by the use of chiral building blocks. The invention further relates to a process for the preparation of a starting compound for the reaction with a chiral building block.

Various biologically active substances, which may be used, for example, in pharmaceutical compositions for human or veterinary application, contain a chiral centre in their molecular structure and therefore give rise to optical isomerism. It is generally known in the art, that often only one of the enantiomers presents the desired optimum biological activity. The presence of the other optical antipode in a composition or agent may cause or invigorate certain side effects and burden the recipient, i.c. the human or animal body. It is generally deemed more and more desirable to administer the biologically active substance in the form of a substantially pure enantiomer, which specifically exhibits the desired biological activity. Therefore, the preparation of substantially enantiopure compound is often an important step in the preparation process of pharmacologically active substances. In most of the cases the enatiomers are obtained by resolution of a racemate into its enantiomers.

There are several methods available to resolve racemates into their respective enantiomers. The first of these, viz. a resolution based on difference in physical properties, e.g. in crystal structure, is only occasionally applicable. The second and by far most generally used method of resolution involves a reaction with a—commercially available—optically active reagent to produce diastereomers, which differ in physical properties. So, the diastereomers obtained in this manner can be separated, e.g. by recrystallization, after which the respective enantiomers can be regenerated by a chemical after-treatment. It will be evident, that such a method of resolving racemates is both labour-intensive and expensive, i.a. on account of the use and recovery of an expensive optically active reagent.

Recently, in a more economical third method of resolution, enzymes are applied to chemically modify one enantiomer of a racemate selectively, followed by a separation of the modified from the unmodified enantiomer. As an example, Bianchi et al. (J. Org. Chem., 1988, 53, 5531–5534) have reported the use of carboxylic anhydrides as acylating agents in lipase-catalysed selective esterification of racemic alcohols. An improvement of this method is described in the European Patent Application 0605033.

Another method for the production of enantiomers is the use of chiral building blocks. In comparison with the first three mentioned methods, this method has the big advantage that the reaction can be carried out in such a way that only or mainly the desired enantiomer is formed. This prevents the formation of substantial quantities (up to 50%) of the undesired enantiomer, a compound that generally has to be considered as chemical waste or, in the case that racemisation is possible, has to be recycled by one or more laborious steps.

It is the objective of the present invention to provide an economically operative process for the stereoselective preparation of a heterocyclic alcohol enantiomer, suitable as an intermediate in the synthesis of pharmacologically active substances such as flesinoxan.

This objective can be achieved by a process using a chiral building block for the introduction of the chiral centre, which process is characterized according to the present invention, in that a substantially pure enantiomer of the general formula

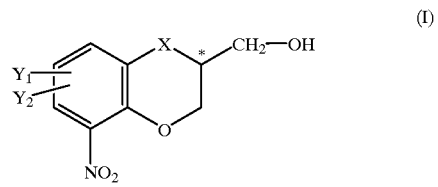

(I)

wherein X is O, S, NH or N-($C_1$–$C_4$)alkyl;
$Y_1$ and $Y_2$ are each independently hydrogen or substituents selected from halogen, ($C_1$–$C_4$)alkyl, ($C_1$–$C_4$) alkoxy, ($C_1$–$C_4$)-haloalkyl, formyl, nitro and cyano;
the C*-atom has either the R or the S configuration;
is prepared from a compound of the general formula

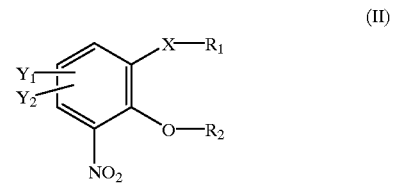

(II)

wherein:
X, $Y_1$ and $Y_2$ have the same meanings as defined above;
$R_1$ is hydrogen or a suitable protective group;
$R_2$ is hydrogen;
or wherein $R_1$ and $R_2$ together form an optionally mono- or di-($C_1$–$C_3$)alkyl substituted methylene bridge;
by the following successive reaction steps:
(i) reaction with a compound of the general formula

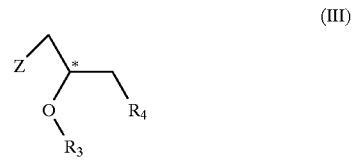

(III)

wherein:
Z is a hydroxy group or a suitable leaving group;
$R_3$ is a hydroxy-protective group;
$R_4$ is a halogen atom;
or wherein $R_3$ and $R_4$ together constitute a valence bond or a biradical of the formula —C($R_{11}$)$_2$—O—, wherein $R_{11}$ is straight or branched ($C_1$–$C_4$)alkyl;
the C*-atom has either the R or the S configuration;
after which reaction a compound is formed of the general formula

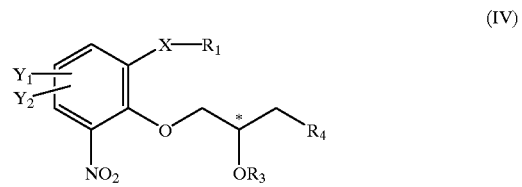

(IV)

wherein:
X, $Y_1$, $Y_2$, $R_3$ and $R_4$ have the above meanings; and

R₁ is hydrogen or a protective group;

(ii) subjection of the compound formed to a deprotection/ring-closure reaction;

(iii) optionally deprotection of the hydroxy group of the ring-closed product.

The protection of a hydroxy group by a suitable protective group is well known in the art, e.g. as described in the Handbook "Protective Groups in Organic Synthesis" by Greene and Wuts (J. Wiley & Sons, Inc., N.Y., 2nd ed. 1991). Examples of suitable protective groups are optionally substituted benzyl, acetyl, butanoyl, optionally substituted benzoyl (e.g. 2,6-dichlorobenzoyl), methoxy isopropyl (MIP), tert. butyl dimethylsilyl and tetrahydropyranyl. Preferred for protective group R₁ are optionally substituted benzyl and benzoyl. Preferred for protective group R₃ is MIP.

The reaction step (i) between the compounds II and III can be carried out in a homogeneous solvent system, in polar solvents as N-methylpyrrolidone (NMP), DMSO and DMF or in a heterogeneous apolar solvent/water system with the aid of a phase transfer catalyst and under the influence of a base. The preferred apolar solvent is toluene. Phase transfer catalysts that can be used are tetrabutylammonium salts, preferably tetrabutylammonium hydrogen sulphate. Examples of bases that can be used are K₂CO₃, NaOH and NaH.

When R₂ is hydrogen, the group Z in compound III has to be a suitable leaving group. Examples of suitable leaving groups are halo and sulphonate leaving groups, such as halogen, mesyloxy, tosyloxy and nosyloxy. The preferred leaving group is the nosyloxy group. When R₁ and R₂ together form a methylene bridge, Z may be hydroxy.

When the compound IV has been formed, a deprotection/ringclosure reaction (ii) is needed in order to form the ring-closed product. Removal of all protective groups is necessary. Deprotection of protected groups can be achieved by methods known in the art. The protecting groups can be removed at the same time or successively, dependent on the nature of the protective group. In the case of an ester protective group, basic conditions can be applied, leading to deprotection of both groups and successive ring-closure to the bicyclic moiety. In the case of MIP protection or when R₃ and R₄ together form a biradical of the formula —C(R₁₁)₂—, wherein R₁₁ has the above defined meaning, the protective group can be removed by acidic conditions as e.g. 45% HBr in acetic acid. The ring-closure reaction is performed by application of basic conditions.

In a suitable embodiment of the method of the present invention, a substantially pure enantiomer of the above general formula I, wherein X is O, is prepared by the above method, characterized in that a substantially pure enantiomer of the general formula I as defined above, wherein X is O, is prepared by reaction of a catechol derivative of the general formula (V)

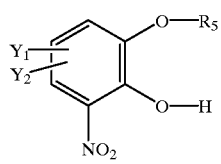

wherein:
Y₁ and Y₂ have the meanings given above; and
R₅ is a suitable hydroxy-protective group;

with a compound of the general formula (VI)

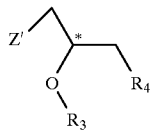

wherein:
R₃ and R₄ have the above meanings; and
Z' is a halo or a sulphonate leaving group, preferably selected from tosyloxy, nosyloxy and mesyloxy;

after which reaction the intermediate obtained, having the general formula (VII)

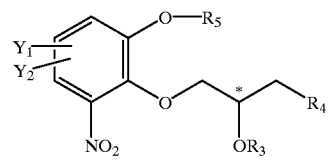

is subjected to the successive reaction steps ii) and iii) as defined above.

Suitable chiral building blocks of the general formula VI for performing the above reaction can be depicted by the following formulas:

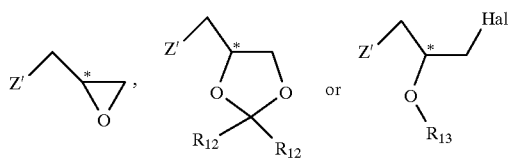

wherein:
C* has either the R or the S configuration;
Z' has the above meaning, and is preferably nosyloxy or tosyloxy;
R₁₂ is (C₁–C₄)alkyl, preferably methyl or isopropyl; and
R₁₃ is a suitable hydroxy-protective group, preferably a methoxyisopropyl (MIP) group.

Preferred conditions for the reaction of the compound of formula V with the above chiral building blocks are: an organic solvent or solvent mixture, such as toluene, methyl isobutyl ketone (MIBK) or a toluene-DMF mixture; reaction temperature between ambient temperature and reflux, preferably reflux; presence of a base, such as NaOH, KOH, K₂CO₃ or NaH (at least equimolar); and, if desired, the presence of a phase-transfer agent. Suitable phase-transfer agents are quaternary ammonium salts, such as tetrabutylammonium hydrogen sulphate and tetrabutylammonium bromide.

Suitable protecting groups are defined above. As for R₁, preferred for protective group R₅ are optionally substituted benzyl and benzoyl. Most preferred is optionally substituted benzyl. In this case the deprotection of R₅, simultaneously with epoxide or solketal cleavage, is preferably carried out in the presence of a mineral acid, such as HCl or HBr, in a polar solvent or solvent mixture, such as acetic acid or acetic acid/NMP, at a temperature between ambient temperature and reflux. The subsequent ring-closure reaction can be performed in the same solvent, preferably under the influence of a suitable base, such as KOH, NaOH, etc.

In another, equally attractive embodiment of the present invention, a substantially pure enantiomer of the general formula I as defined above, wherein X is O, is prepared by reaction of a catechol derivative of the general formula

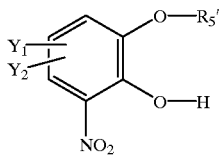
(Va)

wherein:

$Y_1$ and $Y_2$ have the meanings given in claim 1; and $R_5'$ is a hydroxy-protective group selected from the group consisting of $(C_1-C_8)$alkylcarbonyl and arylcarbonyl, wherein the aryl group is optionally substituted with one or more substituents selected from the group consisting of $(C_1-C_4)$alkoxy and halogen;

with a compound of the general formula

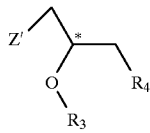
(VI)

wherein:

$R_3$ and $R_4$ have the above meanings; and $Z'$ is a halo or a sulphonate leaving group, preferably selected from tosyloxy, nosyloxy and mesyloxy;

after which reaction the intermediate obtained, having the general formula

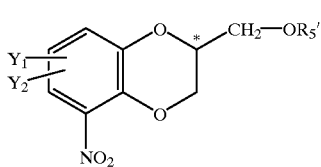
(VIIa)

is subjected to deprotection of the hydroxy group of the ring-closed product.

Suitable chiral building blocks of the general formula VI and preferred reaction conditions are the same as for the reaction of compounds with the general formula V, described above. Preferred hydroxy-protective groups $R_5'$ in this reaction are arylcarbonyl groups. The removal of the hydroxy-protective group $R_5'$ is performed in a manner known in the art.

In another suitable embodiment of the method of the present invention, a substantially pure enantiomer of the above general formula I, wherein X is NH or N-$(C_1-C_4)$alkyl, is prepared by a method as described above, characterized in that a substantially pure enantiomer of the general formula I as defined above, wherein X is NH or N-$(C_1-C_4)$alkyl, is prepared by reaction of a compound of the general formula

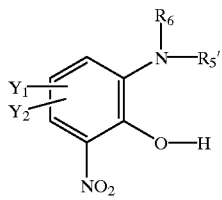
(VIII)

wherein:

$Y_1$ and $Y_2$ have the meanings given above; and $R_5'$ is a suitable amino-protective group;

$R_6$ is hydrogen or $(C_1-C_4)$alkyl;

with a compound of the general formula

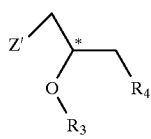
(VI)

wherein:

$R_3$ and $R_4$ have the above meanings; and $Z'$ is a halo or a sulphonate leaving group, preferably selected from tosyloxy, nosyloxy and mesyloxy;

after which reaction the intermediate formed, having the general formula

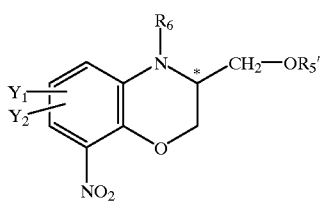
(X)

is subjected deprotection of the hydroxy group of the ring-closed product.

Examples of suitable amino-protective groups are acyl groups, such as arylcarbonyl, alkylcarbonyl (e.g. acetyl) and alkylsulfonyl groups. Preferred are alkylcarbonyl groups. The reaction steps can be performed as described above for the formula I compounds wherein X is O.

In another, equally attractive embodiment of the method of the present invention, a substantially pure enantiomer of the above general formula I, wherein X is O, can be prepared by reacting a benzodioxole compound of the general formula

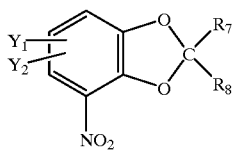
(XI)

wherein:

$Y_1$ and $Y_2$ have the meanings given above; and $R_7$ and $R_8$ are each independently hydrogen or methyl;

with, as a chiral building block, a compound of the formula

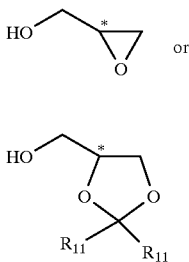

(XIIa)

or (XIIb)

wherein:
$R_{11}$ is straight or branched $(C_1-C_4)$alkyl.

This reaction is preferably carried out in a polar organic solvent, such as DMF, DMSO, NMP or toluene, in the presence of a base, such as NaOH, KOH, NaH or $K_2CO_3$, at a reaction temperature between 0° C. and reflux. In the case of the use of a compound of the formula XIIb, the subsequent solketal ring cleavage and the ring-closure reaction to the formula I (X=O) compound is performed as described above, viz. by a treatment with mineral acid in e.g. acetic acid, followed by a treatment with aqueous base, e.g. an aqueous NaOH-solution.

The invention also relates to compounds to be used as new intermediates in the method as described above, such compounds having the general formula

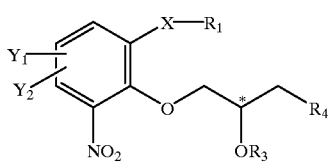

(IV)

These new compound can be prepared as described above, viz. by a method of preparing a compound as defined above, characterized in that a compound of the general formula

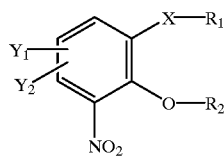

(II)

wherein the symbols have the meanings given above; is reacted with a compound of the general formula

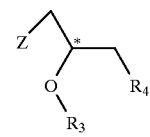

(III)

wherein the symbols also have the meanings given above.

Furthermore the invention also relates to compounds to be used as new intermediates in the method described above, such compounds having the general formula

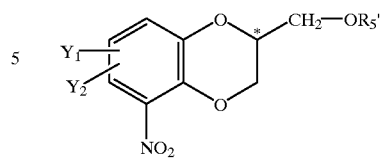

(VIIa)

wherein the symbols have the meanings given above. These new compounds can be prepared as described above, viz. by a method of preparing a compound as defined above, characterized in that a compound of the general formula

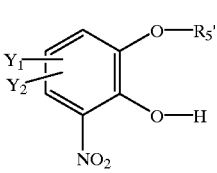

(Va)

wherein the symbols have the meanings given above; is reacted with a compound of the general formula

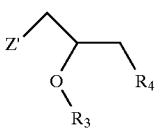

(VI)

wherein the symbols also have the meanings given above.

For the above-mentioned reaction V+VI→VII, a suitable monohydroxy-protected catechol derivative of formula V is required as a starting compound. Suitable protecting groups are alkylcarbonyl groups (e.g. acetyl), (optionally substituted) benzyl groups and trialkylsilyl groups.

The preparation of monoacetates of hydroquinone and catechol has been investigated, according to early publications, with varying results. Oltcott (J. Am. Chem. Soc. 59, 1937, 392–393) has found, that the monacetylation of these two dihydroxybenzenes can be performed by careful reaction with an acetylating agent, e.g. acetic anhydride, in aqueous alkaline solution. The desired mono-acetate was obtained in a yield of only 20–30%, whereas the major product obtained was the diacetate. Johnston (Chem. Ind. 1982, 1000) has succeeded in improving the formation of the mono-acetate of hydroquinone from hydroquinone and acetic anhydride by using triethyl amine as a base and 4-dimethylaminopyridine (DMAP) as a catalyst, in a polar organic solvent, viz. in ethyl acetate solution. Under such reaction conditions, Johnston has succeeded in obtaining hydroquinone mono-acetate in yields of 58–65%.

It will be obvious that the above results are also not attractive from an economical point of view for the production of mono-protected dihydroxybenzenes.

It has now been found, as an additional aspect of the present invention, that mono-protected catechol derivatives having the general formula

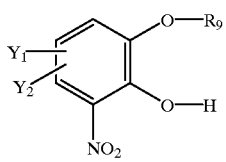

(XIV)

wherein:
Y$_1$ and Y$_2$ have the meanings given above, and
R$_9$ is an optionally substituted benzoyl group, a (C$_1$–C$_4$) alkylcarbonyl group or a tri(C$_1$–C$_4$)alkylsilyl group;
can easily be prepared in high yields by reaction of a substituted catechol of the general formula

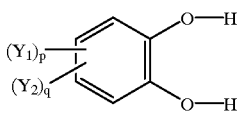

(XIV)

wherein:
Y$_1$ and Y$_2$ have the above meanings, and
p and q are 0 or 1;
with a compound of the general formula (R$_9$')$_2$O or R$_9$'Hal or (R$_{14}$)$_3$SiHal wherein:
R$_9$' is an optionally substituted benzoyl group or a (C$_1$–C$_6$)alkyl-carbonyl group;
R$_{14}$ is (C$_1$–C$_4$)alkyl; and
Hal is halogen;
in the presence of an organic base, preferably a tert. amine or a mixture of organic bases, in a catalytic amount; characterized in that the reaction is carried out in an apolar organic solvent or without a solvent, after which the compound obtained, having the general formula

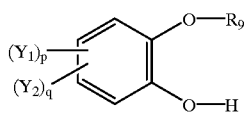

(XVIa)

is successively subjected to an aromatic substitution reaction to introduce substituents Y$_1$ and Y$_2$ into the aromatic nucleus, if necessary, and to a nitration.

When an acyl protecting group is desired, the mono-acylation reaction is preferably carried out without a solvent, so in a melt, if the reaction mixture is liquid under the reaction conditions applied. The reaction temperature may vary between ambient temperature and approx. 150° C., dependent on the character of the reaction components; in general a slightly elevated reaction temperature is used. The reaction may also be carried out in an apolar organic solvent, such as a hydrocarbon, e.g. toluene and xylene, or a dialkyl ether, e.g. methyl tert.-butyl ether (MTBE). Suitable organic bases for the above monoprotection of catechol are amines, such as triethyl amine (TEA), diethyl amine, triisobutyl amine (TIBA), pyridine, 2,6-lutidine, dimethyl aniline (DMA), DMAP, and mixtures of DMAP with TEA or TIBA.

For the above mono-acylation the amine should be present in an at least catalytic amount based on the starting catechol; the starting acylating agent is preferably present in a slight equimolar excess. The mono-acylation of catechol can so easily be realized in yields of over 85%, based on starting catechol.

For the formation of the catechol mono(trialkylsilyl)ether various trialkylsilyl halides can be used, such as a tert.-butyl dimethylsilyl halogenide. This reaction can easily be performed in an apolar organic solvent, such as a dialkyl ether, e.g. methyl tert.-butyl ether, in the presence of an equivalent amount of an organic base as defined above. At elevated temperature, e.g. at reflux, the desired monosilyl ether of catechol can be obtained in a yield of over 90%.

Monoprotection can also be realized by monobenzylation. For the formation of a monobenzyl protected catechol an (optionally substituted) benzylhalogenide, preferably (optionally substituted) benzylchloride is used as a reagent in the presence of a base. Suitable solvents are alcohols. The preferred solvent is methoxyethanol. Alternatively a two phase hydrocarbon/water system, preferably toluene/water, can be used with the aid of a phase transfer catalyst e.g. a tetra-alkylammonium salt. A second alternative is the mono-alkylation without a solvent in the presence of a phase transfer catalyst. Usefull bases are hydroxides and carbonates, such as NaOH, KHCO$_3$ and K$_2$CO$_3$. The addition of a catalytic amount of an iodide can be usefull in order to improve the reaction rate. In this way a mono-alkylation of catechol can be realized in yields over 80%.

The subsequent introduction of substituents Y$_1$ and Y$_2$ if these substituents are not yet present during the monoprotection of catechol, as well as the following nitration, is carried out by methods known in the art. The electrophilic aromatic substitution for introducing Y$_1$ and Y$_2$ is well-known in the art; a chlorination, for example, can easily be performed with a suitable chlorination agent, such as sulphuryl chloride, etc. The final nitration can equally be performed according to well-known methods, e.g. by using concentrated nitric acid. For both aromatic substitutions acetic acid is a suitable solvent. If for the monoprotection of catechol a mono-acylation in a melt reaction (without a solvent) is chosen, the subsequent introductions of Y$_1$ and Y$_2$, if necessary, and of NO$_2$ can easily be carried out as an one-pot reaction without isolating intermediates.

The present invention further relates to an intermediate to be used in the method as defined hereinbefore, viz. intermediates of the general formula

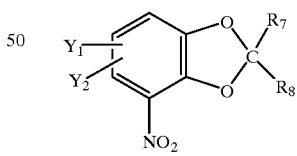

(XI)

This intermediate of formula XI can be prepared from a catechol of above formula XV by the following process steps:
(i) selective protection of one of the free hydroxy groups;
(ii) optional introduction of one or both of the substituents Y$_1$ and Y$_2$;
(iii) selective nitration of the position ortho to the unsubstituted hydroxy group;
(iv) deprotection of the protected hydroxy group;
(v) formation of the benzodioxole moiety by reaction with a compound of the general formula (XVII)

wherein:

$R_7$ and $R_8$ have the meanings given above;

$R_9$ and $R_{10}$ are each individually chlorine, bromine or $(C_1-C_4)$alkoxy or form together an oxygen atom.

The above reaction steps (i), (ii), (iii) and (iv) have been described hereinbefore. The reaction step (v) is preferably carried out by reacting the substituted catechol, obtained after reaction step (iv) and having the general formula (XVIII)

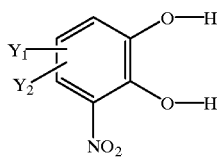

wherein $Y_1$ and $Y_2$ have the above meanings, with a benzodioxole-forming compound of the above formula XVII, preferably by a methylene-donating agent, such as $CH_2Cl_2$ or $CH_2Br_2$, in the presence of an anorganic base, such as NaOH, KOH or $K_1CO_3$, in an organic solvent. Suitable organic solvents for this reaction are DMSO, DMF, NMP and toluene, if desired in the presence of a phase-transfer agent. Best results are obtained in DMF as a solvent or in toluene in the presence of a phase-transfer agent. The reaction proceeds smoothly at elevated temperature, e.g. at reflux.

The invention will now be described in greater detail with reference to the following specific examples.

EXAMPLE I

Mono-Acylation of Catechol

Reaction Scheme:

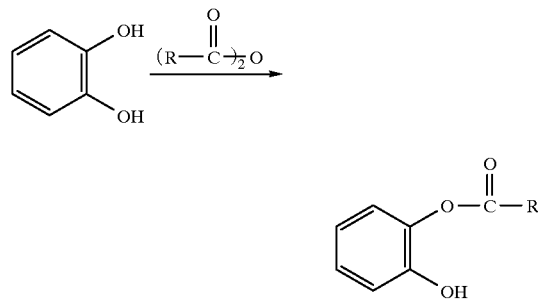

A mixture of 45 mmol catechol and 53 mmol of the acylanhydride is cooled to 2–8° C. in a water/ice bath. Then 1.5 mmol of an organic base is added as a catalyst. The reaction mixture is stirred for 3 hours at ambient temperature. After successive addition of 200 ml ethylacetate and 150 mil water the phases are separated. The organic layer is washed twice with 50 ml 5% aqueous $NaHCO_3$ solution and then twice with 50 ml water. The combined aqueous phase is extracted twice with 50 ml ethylacetate. The organic layers are combined and evaporated to dryness under reduced pressure, yielding the desired mono-acylated catechol. The following results are obtained: with acetic anhydride (without an additional solvent):

| catalyst | yield* (%) |
|---|---|
| triethylamine (TEA) | 90 |
| diisopropylethylamine (DIEA) | 92 |
| triisobutylamine (TIBA) | 93 |
| pyridine | 67 |
| 2,6-lutidine | 91 |
| dimethylaniline (DMA) | 90 |
| 4-dimethylaminopyridine (DMAP) | 84 |
| DMAP/TEA (1/1) | 88 |
| DMAP/TIBA (1/2) | 88 |
| imidazole | 75 |

*Yield measured by GC analysis

In case toluene is used as a solvent for the above TEA-catalyzed reaction, mono-acetyl catechol is obtained in a yield of 86%.

The same above TEA-catalyzed acylation reaction is carried out, using various acylanhydrides; without a solvent except for the monobenzoylation: toluene as a solvent. The following results are obtained:

| acylanhydride | yield* (%) |
|---|---|
| acetic anhydride | 90 |
| propionic anhydride | 90 |
| butyric anhydride | 90 |
| valeric anhydride | 93 |
| isobutyric anhydride | 87 |
| benzoic anhydride | 86 |

*yield measured by GC analysis

EXAMPLE II

Alkylation of Catechol

Reaction Scheme:

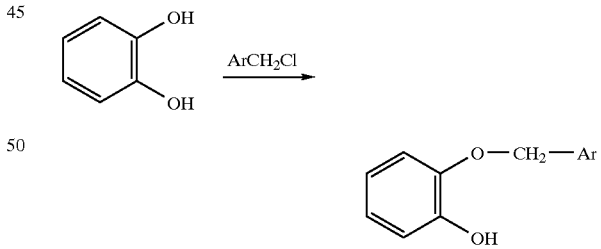

A. Mono-alkylation of catechol in organic solvent

To a mixture of 45 mmol catechol, 58.5 mmol $NaHCO_3$ and 50 ml solvent, 49.5 mmol alkylating agent is added. The mixture is heated to 85° C., while stirring. After a reaction time of 20 hours the reaction mixture is allowed to cool, and successively 200 ml toluene and 150 ml water are added. The layers are separated. The organic layer is washed twice with 50 ml 5% aqueous $NaHCO_3$ solution and then twice with 50 ml water. The combined aqueous phase is extracted twice with 50 ml toluene. The collected organic layers are evaporated to dryness under reduced pressure at approx. 40° C., yielding the desired catechol mono-ether.

The monobenzylation of catechol with benzylchloride is carried out in various solvents, with the following results:

| solvent | yield* (%) |
|---|---|
| ethanol | 78 |
| isopropanol | 72 |
| methoxyethanol | 81 |
| ethyleneglycol/isopropanol (1/4) | 72 |

The above mono-alkylation of catechol is carried out in methoxyethanol as the solvent, starting from various substituted benzylchlorides:

| (substituted) benzylchloride | yield* (%) |
|---|---|
| unsubst. | 77 |
| 4-chloro- | 75 |
| 4-methyl- | 74 |
| 3-chloro- | 72 |
| 3-methoxy- | 76 |
| 2,4-dichloro- | 75 |
| 2-chloro- | 75 |
| 2-fluoro- | 73 |

*Yield measured by GC analysis

B. In the presence of a phase transfer catalyst, in toluene

A mixture of 45 mmol catechol, 4.1 mmol tetrabutylammonium hydrogensulfate (TBAHS) and 25 mmol $K_2CO_3$ in 150 ml toluene is refluxed for 2 hours under azeotropic distillation of water (Dean-Stark device). Then 49.5 mmol of the alkylating agent is added, and the mixture is refluxed for approx. 20 hours while stirring. After allowing the mixture to cool, successively 100 ml toluene and 150 ml water are added. The layers are separated, and the organic layer is washed twice with 50 ml 5% aqueous $NaHCO_3$ solution and then twice with water. The combined water layers are extracted twice with 50 ml toluene. The collected organic layers are evaporated to dryness under reduced pressure at approx. 40° C., to yield the desired catechol mono-ether.

By using benzylchloride as the alkylating agent the desired monobenzyl catechol ether is obtained in a yield of 85%.

C. Mono-alkylation of catechol without a solvent; presence of phase transfer agent A mixture of 45 mmol catechol, 58.5 mmol $KHCO_3$ and 4.5 mmol TBAHS is stirred for 15 min at 115° C. To this mixture is added 49.5 mmol alkylating agent, and the reaction mixture is stirred at 115° C. for 2 hours. After the mixture has been allowed to cool, successively 150 ml ethylacetate and 100 ml water are added. The phases are separated, and the organic layer is washed twice with 50 ml 5% aqueous $NaHCO_3$ and twice with water. The combined aqueous layer is extracted twice with 50 ml toluene. The collected organic layers are evaporated to dryness under reduced pressure at approx. 40° C., yielding the desired mono-alkyl ether of catechol.

Instead of TBAHS tetrabutylammonium bromide and tetrabutyl-ammonium chloride can be used as phase transfer agents. The following results are obtained:

| (substituted) benzylchloride | yield* (%) |
|---|---|
| unsubstituted | 72 |
| 3-chloro- | 71 |
| 4-chloro- | 72 |
| 2,4-dichloro- | 76 |
| 4-nitro- | 70 |

*Yield measured by GC analysis

D. Alkylation of catechol in water

To a mixture of 45 mmol catechol, 58.5 mmol $NaHCO_3$ and 50 ml water is added 49.5 mmol alkylating agent. The mixture is refluxed for 1.5 to 22 hours while stirring. After successive addition of 200 ml ethylacetate and 100 ml water the layers are separated. The organic layer is washed twice with 50 ml 5% aqueous $NaHCO_3$ and twice with water. The combined aqueous layer is extracted twice with 50 ml toluene. The collected organic layers are evaporated to dryness under reduced pressure at approx. 40° C., yielding the desired catechol mono-alkyl ether. The following results are obtained:

| alkylating agent | reflux time (h) | yield* (%) |
|---|---|---|
| benzylchloride | 1.5 | 67 |
| 3-chlorobenzylchloride | 3.5 | 80 |
| 2-chlorobenzylchloride | 6 | 82 |
| 2-fluoro-benzylchloride | 5 | 69 |
| 2,4-dichlorobenzylchl. | 6 | 80 |
| 3-methoxybenzylchloride | 22 | 87 |

*Yield measured by GC analysis

EXAMPLE III

Monosilylation of Catechol

Reaction Scheme:

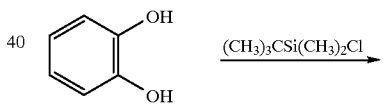

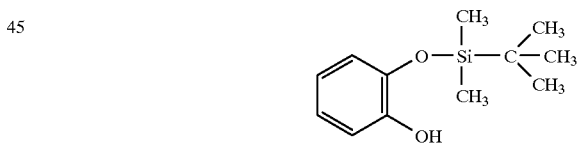

To a mixture of 45 mmol catechol and 54 mmol tert.-butyldimethylsilyl chloride in 50 ml methyl tert.-butyl ether (MTBE) 45 mmol triethylamine is added in 10 min. The reaction mixture is refluxed for 16 hours while stirring and then allowed to cool. After successive addition of 150 ml MTBE and 150 ml water the layers are separated. The organic layer is washed twice with 50 ml 5% aqueous $NaHCO_3$ solution and twice with 50 ml water. The combined aqueous layer is extracted twice with 50 ml MTBE. The collected organic layers are evaporated to dryness under reduced pressure at approx. 40° C., yielding 10.6 g of the desired catechol mono-(trialkylsilyl) ether as a yellow oil with a purtity of 87% (91% yield).

$^1$H-NMR (δ, $CDCl_3$)=0.27 (s, 6H), 1.02 (s, 9H), 6.74 (t, 1H, J=8 Hz), 6.82 (d, 1H, J=8 Hz), 6.86 (t, 1H, J=8 Hz), 6.93 (d, 1H, J=8 Hz).

EXAMPLE IV

Preparation of 5-Chloro-3-Nitrocatechol

Reaction Scheme:

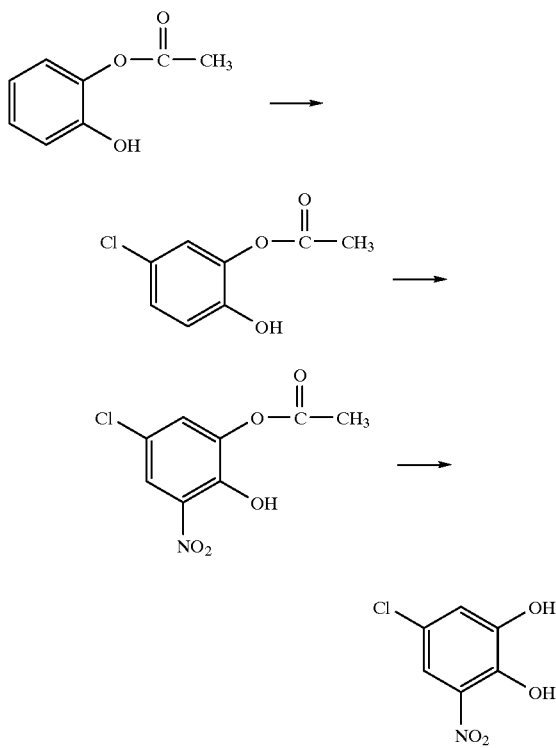

a) Preparation of 3-nitro-5-chloro-mono-acetylcatechol 110 g catechol (1 mol) is dissolved in 110 ml acetic acid. 4.4 ml (0.03 mol) triethylamine and 110 ml (1.19 mol) acetic anhydride is added and the mixture is heated to 80° C. during 60 minutes. After cooling down till 15° C. 330 ml acetic acid is added and 82.5 ml (1.04 mol) surfuryl chloride is dosed in about 25 minutes, keeping the temperature below 15° C., followed by stirring for 40 minutes at 15° C. A solution of 115.5 ml (1.8 mol) of 70% $HNO_3$ in 165 ml of acetic acid is prepared, keeping the temperature below 20° C. To this mixture the above obtained chlorination reaction mixture is dosed in 60 minutes at 15–20° C., followed by an additional stirring for 30 minutes at 15–20° C. 275 ml toluene and 550 ml water are added and the layers are separated. The water layer is extracted with 140 ml of toluene (3×) and the combined organic layers are washed with 140 ml water (4×). The toluene is removed by vacuum distillation, 200 ml of ethanol is added and removed by vacuum distillation. After addition of 275 ml of ethanol, heating the mixture until all material has been solved, cooling down to 0–5° C. under stirring and stirring for an additional hour the crystals formed are filtered, washed with cold ethanol and dried to yield 106.5 g (46%) of 99% pure 3-nitro-5-chloro-mono-acetylcatechol.

$^1$H-NMR: ($\delta$, DMSO/$CDCl_3$=3/1)=7.07 (d, 1H, J=2 Hz), 7.34 (d, 1H, J=2 Hz).

b) Preparation of 3-nitro-5-chloro-catechol

The crystallate obtained above is suspended in 200 ml water. In 15 minutes 82 ml 50% NaOH is added under stirring, keeping the temperature below 30° C., followed by an additional stirring of 15 minutes. In ten minutes 155 ml concentrated hydrochloric acid is added, keeping the temperature below 35° C., followed by cooling down to 25° C. 135 ml methyl-t-butyl ether (MTBE) is added and the mixture is stirred for 15 minutes, followed by separation of the layers. The water layer is extracted twice with MTBE. The combined organic layers are concentrated by evaporation to yield a 85.6 g (45% calculated on starting catechol) of a yellow, solid product with a purity of 99%.

EXAMPLE V

Synthesis of 6-Chloro-4-nitro-1,3-benzodioxole

Reaction Scheme:

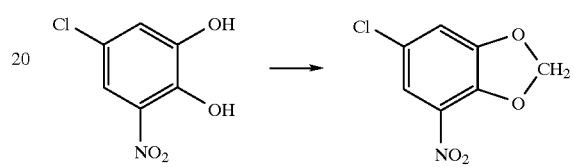

5-Chloro-3-nitro-catechol can be prepared in two manners, viz. (1) from salicylaldehyde, by a successive chlorination, nitration and Dakin oxidation according to the method dexcribed by M. Nikaido et al., J. Org. Chem. 1984, 49, 4740–1, or by starting from monoprotected catechol as described in Example I.

(a) Synthesis of the title compound by using $CH_2Cl_2$

Under $N_2$ 8.0 g of NaOH (powdered) is dissolved in 80 ml of DMSO, or, alternatively, in N-methylpyrrolidone (NMP) at 80° C. In about 15 min a solution of 20.0 g of 5-chloro-3-nitro-catechol in 20 ml DMSO (NMP) and 100 ml $CH_2Cl_2$ is added at 80° C. The reaction mixture is heated at 130° C. for 8–30 hours while stirring. After cooling down to room temp., successively 200 ml water and 400 ml toluene are added. Stirring for 5 min., separation of the layers, and extraction of the water layer with 100 ml toluene yields a combined organic phase, which is washed twice with 50 ml satd. aqueous NaCl solution, with 50 ml water and twice with 100 ml satd. aqueous NaCl solution. After evaporation of the solvent (100 mbar, 40° C.), the desired product is obtained in a yield of 70.3%; purity 84%.

$^1$H-NMR ($\delta$, DMSO/$CDCl_3$=4/1)=6.39 (s, 2H), 7.46 (d, 1H, J=2 Hz), 7.58 (d, 1H, J=2 Hz).

(b) Synthesis of the title compound by using $CH_2Br_2$

Under $N_2$ 200 g of 5-chloro-3-nitro-catechol is dissolved in 1050 ml DMF. To this solution are added 204 g anhydrous, powdered $K_2CO_3$ and 220 ml $CH_2Br_2$, while stirring the mixture. The reaction mixture is refluxed for 1 hour (140° C.) and then cooled down to 80° C. After addition of 800 ml water, the mixture is cooled down to room temp. The crystalline product is filtered off and washed successively with 2×600 ml water, 2×250 ml ethanol, and 2×300 ml n-hexane. After drying under reduced pressure at 60° C., the desired product is obtained in a yield of 82%; purity 95%. Equally successful results are obtained in toluene as the solvent instead of DMF, under phase transfer conditions.

EXAMPLE VI

Conversion of Monoprotected Chloro-Nitrocatechol to Compound with Formula VII

Reaction Scheme:

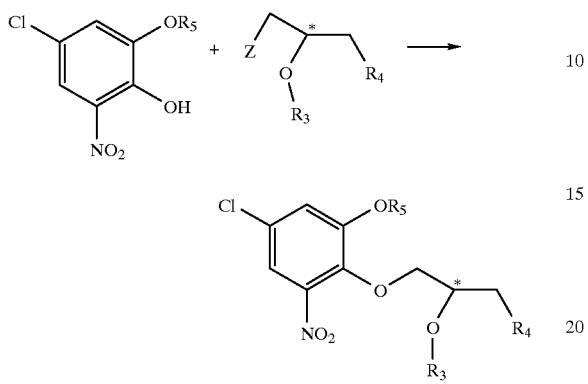

(a) Reaction with enantiomerically pure glycidyl compounds (Z is nosyl; $R_3$ and $R_4$ together form a valence bond; $R_5$ is benzyl)

5-Chloro-3-nitro-monobenzylcatechol (8.94 mmol), $K_2CO_3$ (9.78 mmol), TBAHS (23 mol %) and 100 ml toluene are stirred under reflux during 30 minutes under simultaneous removal of water (Dean-Stark device). The mixture is cooled to 80° C. and (R)-glycidylnosylate (8.94 mmol) is added. The mixture is stirred at 100° C. during 30 minutes, cooled down and diluted with ethylacetate/brine. The water layer is extracted with ethyl acetate two times. The combined organic layers are washed with brine (2×), dried over $MgSO_4$ and filtered over 30 g of silica. The filter is washed with ethyl acetate and the filtrate is reduced by evaporation. The residue is crystallized from 20 ml 96% ethanol, yielding 2.7 g (90%) yellowish needles with an ee>97% (determined with NMR).

$^1$H-NMR (δ, $CDCl_3$)=2.61 (dd, 1H, J=5 Hz, J=3 Hz), 2.80 (dd, 1H, J=5 Hz, J=5 Hz), 3.33 (cluster, 2H), 4.24 (m, 1H), 5.13 (s, 2H), 7.15 (d, 1H, J=2 Hz), 7.36 (d, 1H, J=2 Hz), 7.37–7.48 (cluster, 5H).

The same reaction is carried out in a solvent mixture of DMF/toluene 1/1 without a phase transfer agent. After 18 hours at 110° C. the desired product is obtained in a yield of 73%; ee=98%.

A corresponding experiment starting from (R)-glycidyltosylate, in toluene and with TBAHS, yields after 46 hours 82% of the desired product; ee=98%.

The corresponding (S)-glycidyl ether of 5-chloro-3-nitro-monobenzyl-catechol is obtained by a corresponding reaction of the starting mono-protected catechol with (S)-glycidyltosylate in toluene in the presence of TBAHS. Yield, after 15 hours, 77%; ee=98%. In a DMF/toluene (1/1) mixture without TBAHS the same product is obtained (ee=98%) after 46 hours in a yield of 73%.

(b) Derivatization of 5-chloro-2-hydroxy-3-nitrophenol-benzylether with a solketal compound (Z is nosyl; $R_3$ and $R_4$ together constitute a biradical of the formula —$C(CH_3)_2$—O—; $R_5$ is benzyl)

In a corresponding manner as described under (a) the solketal ether of 5-chloro-3-nitro-monobenzylcatechol is prepared: 1.1–1.2 eq. $K_2CO_3$, 10 mol % TBAHS, toluene, reflux. By using (S)-solketal-nosylate the desired (S)-solketal ether of 5-chloro-3-nitro-monobenzylcatechol is obtained in a yield of 83%; ee=98%.

The corresponding (R)-solketal ether is obtained by using the (R)-solketal-tosylate in a yield of 68% after a reaction time of 38 hours; ee=98%. The yield can be improved to 80% after 49 hours reflux.

(c) Derivatization of 5-chloro-2-hydroxy-3-nitrophenol-benzylether with the methoxy isopropyl ether of 1-chloro-3-tosyloxypropan-2-ol (TCA-MIP ether) (Z is tosyl; $R_3$ is $C(CH_3)_2OCH_3$); $R_4$ is chloro; $R_5$ is benzyl)

In a corresponding manner as described under (a) the above compound is prepared from 5-chloro-3-nitro-monobenzylcatechol and chiral TCA-MIP ether; $K_2CO_3$, TBAHS, toluene, 24 hours reflux. The desired enantiomerically pure product is obtained in a yield of 53%.

EXAMPLE VII

Conversion of monoprotected chloro-nitrocatechol to compound with formula VIIa

Reaction Scheme:

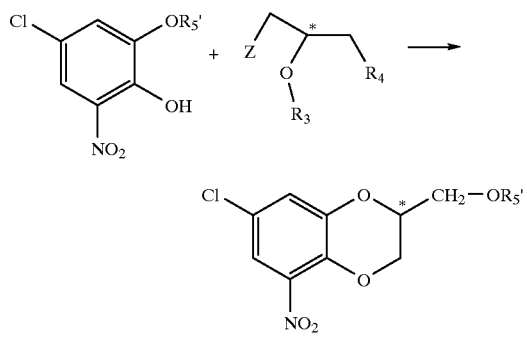

Reaction with enantiomerically pure glycidyl compounds (Z is nosyl; $R_3$ and $R_4$ together form a valence bond; $R_5$' is benzoyl).

(a) Preparation of (S)-7-chloro-2,3-dihydro-5-nitro-benzodioxin-2-methanol benzoic ester 2.0 g 5-chloro-3-nitro-mono-benzoylcatechol (6.3 mmol), 0.9 g $K_2CO_3$ (6.3 mmol) and 0.2 g TBAHS (0.63 mmol) are suspended in 75 ml toluene and refluxed under simultaneous removal of water (Dean Stark device). After removal of 25 ml toluene the orange mixture is cooled to 60° C. and 1.7 g S(+)-nosyl glycidyl ester is added. After refluxing during 23 hours the reaction mixture is diluted with saturated brine (10 ml) and water (10 ml) and extracted with 50 ml ethyl acetate. The organic layer is washed with 10 ml saturated brine (2×) and with acidified water (2×(15 ml $H_2O$ and 2.5 ml 2N HCl)). The organic layer is reduced by evaporation to yield 2.52 g of an orange/brown syrup. The syrup is puriefied by flash chromatography over a 4.0×30 cm column of silica gel with petroleum ether/diethylether (1/1). The product (S)-7-chloro-2,3-dihydro-5-nitro-benzodioxin-2-methanol benzoic ester is obtained as a yellow solid: 0.75 g (68%); M.p.=83–88° C.; ee=96%; $[\alpha]_D^{25}$=+110.3 (EtOAc, c=10 g/l, d=20 cm).

$^1$H-NMR (δ, $CDCl_3$)=8.02 (dd), 7.60 (t), 7.52 (d), 7.46 (t), 7.17 (d), 4.62 (m), 4.27 (dd).

EXAMPLE VIII

Conversion of Aminoprotected Chloro-Nitro-Aminophenol to Compound with Formula X Reaction Scheme:

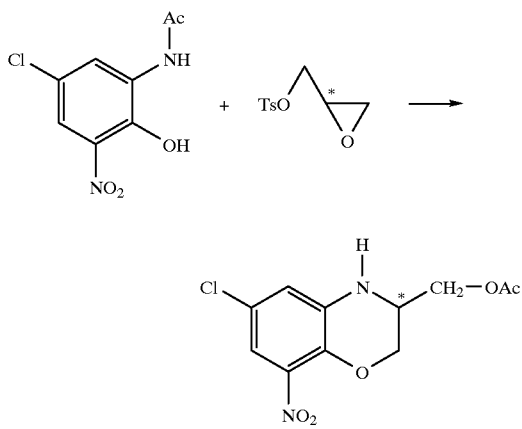

A suspension of N-acetyl-2-hydroxy-3-nitro-5-chloro-aniline (34.6 mmol), $K_2CO_3$ (40.6 mmol), 80 ml NMP and 80 ml toluene is refluxed during one hour under removal of water (Dean Stark device). The toluene is distilled off and the reaction mixture is cooled down to 110° C. (S)-glycidyltosylaat (40.8 mmol) is added. The reaction mixture is stirred at 120° C. during 4.5 hours, followed by cooling and dilution with water and ethylacetate and coorecting the pH to 4 to 6 with diluted hydrochloric acid. The water layer is extracted twice with ethylacetate. The combined organic layers are washed three times with brine and dried over $MgSO_4$. After filtration and evaporation of the solvent under reduced pressure, 10.8 g of a dark brown oil is obtained. After chromatography over $SiO_2$ (ethylacetate/petrol ether 1:3) 3-acetoxymethyl-6-chloro-8-nitro-2,3-dihydro-1,4-benzoxazine is obtained in a yield of 42%. ee=86%. $[\alpha]_D^{20}$=−11,6 (c=0,86, 96% ethanol), mp 76–84° C.

$^1$H-NMR (δ, $CDCl_3$)=2.12 (s, 3H), 3.79 (m, 1H), 4.07–4.35 (cluster, 4H), 4.58 (broad s, 1H, NH), 6.78 (d, 1H, J=2 Hz), δ 7.21 (d, 1H, J=2 Hz).

EXAMPLE IX

Derivatization, Starting from Substituted 1,3-Benzodioxole (a) Reaction with solketal derivatives Reaction Scheme:

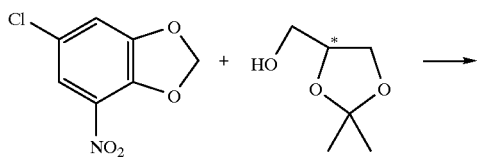

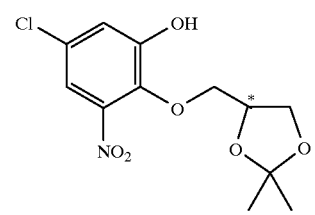

6-Chloro-4-nitro-1,3-benzodioxole is derivatized by a reaction with chiral solketal, i.e. chiral 4-hydroxymethyl-2,2-dimethyl-1,3-dioxolan. The reaction is performed in a suitable organic solvent, such as DMF, NMP or toluene, in the presence of a base, e.g. $K_2CO_3$, $Li_2CO_3$, NaH, etc. If toluene is used as a solvent, a phase transfer agent is additionally preferred, e.g. TBAB or TBAHS.

So, 4.6 g (3 eq) powdered $K_2CO_3$ is suspended in 20 ml DMF under nitrogen at room temperature. 1.46 ml S-solketal (1 eq) is added to this suspension, followed by a solution of 2.2 g 6-chloro-4-nitro-1,3-benzodioxole in 20 ml DMF. The mixture is heated to 90° C. during 70 hours. After cooling down to room temperature 50 ml toluene and 50 ml saturated NaCl solution are added, and the mixture is stirred during 5 minutes. The pH is adjusted to 5–6 with about 15 ml of 2N HCl solution. The layers are separated and the water layer is extracted (2×) with 25 ml toluene. The concentrated organic layers are washed (3×) with 25 ml saturated NaCl solution. The organic layer is concentrated to evaportion to yield 3.27 g (92%) (S)-(4-chloro-2-hydroxy-6-nitro)-phenoxymethyl-2,2-dimethyl-1,3-dioxolan.

$^1$H-NMR (δ, $CDCl_3$): 1.48 (s, 3H), 1.54 (s, 3H); 3.91 (t, 1H, J~8 Hz), 4.08 (dd, 1H, J~6 Hz, J~11), 4.18 (t, 1H, J~8 Hz), 4.37 (dd, 1H, J=11 Hz, J=3 Hz), 4.52 (m, 1H), 7.18 (d, 1H, J=2 Hz), 7.36 (d, 1H, J=2 Hz), 8.74 (s, 1H).

After a reaction time of 5 hours in NMP as the solvent the same product can be obtained in a yield of 79%.

The corresponding (R)-solketal ether is prepared in a corresponding manner, using (R)-solketal as the starting material.

In a corresponding manner enantiopure 4-chloro-2-hydroxy-6-nitro-phenoxymethyl-2,2-diisopropyl-1,3-dioxolan compounds can be obtained starting from 6-chloro-4-nitro-1,3-benzdioxole and chiral 4-hydroxymethyl-2,2-diisopropyl-1,3-dioxolan.

(b) Reaction with glycidol

Reaction Scheme:

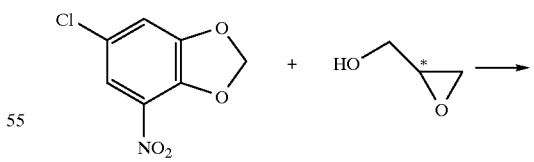

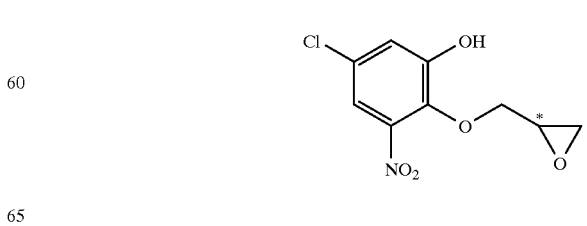

A solution of 6-chloro-4-nitro-1,3-benzodioxole (2.48 mmol) in 10 ml DMF is cooled down in an icebath. A 60%

NaH dispersion (5.5 mmol) in mineral oil is added, immediately followed by a solution of (S)-glycidol (3.13 mmol, ee=84%) in 5 ml DMF. After 1,5 hours stirring at 0° C. ice is added ice together with brine and 2N HCl until the pH is lower then 5. The water layer is extracted three times with ethylacetate. The combined organic layers are washed three times with brine, dried on MgSO$_4$ and filtrated. After filtration over Al$_2$O$_3$ and evaporation of the solvent under reduced pressure, 0.4 g of a dark brown oil is obtained. (S)-7-chloro-2,3-dihydro-5-nitro-benzodioxin-2-methanol is obtained in a yield of 35% after chromatography over SiO$_2$. ee=74%.

EXAMPLE X

Deprotection and Ring-Closure; Formation of Subst. Benzodioxin-2-Methanol and Related Compounds Reaction Scheme:

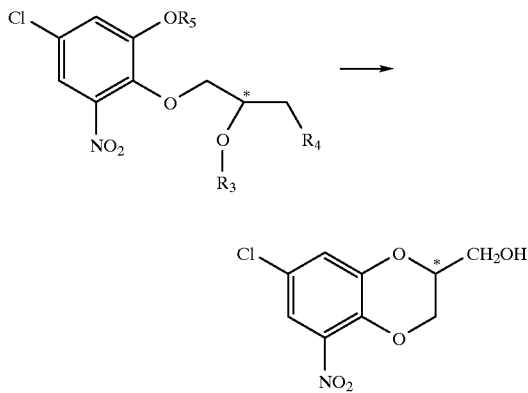

(a) The product prepared in Example VI under (a) is deprotected under simultaneous epoxide ring-opening by mineral acid. The chloro-nitro-monobenzyloxyphenyl (R)-glycidyl ether can be converted easily to the corresponding catechol monochlorohydrine by reflux in a propanol/water (1/1) mixture during 48 hours under the influence of 30 eq. HCl; yield 87%; ee=98%; after 3 hours reflux the deprotection is already 83%. The corresponding (S)-enantiomer is formed in 83% yield (ee=86%) after 9 hours reflux. Alternatively, acetic acid can be used as the solvent. Then the deprotection and epoxide ring-opening proceed smoothly already at 35° C. in 1 hour.

The above chlorohydrine is ring-closed under basic conditions, yielding the desired chiral 7-chloro-2,3-dihydro-5-nitro-benzodioxin-2-methanol in quantitative yields. The ring-closure is easily carried out in ethanol/water (1/1) as the solvent at room temp. under the influence of approx 2 eq. of NaOH or KOH; reaction time approx. 18 hours.

(b) Deprotection and ring closure of the solketal ether obtained according to Example VI(b)

The deprotection is carried out in a suitable solvent or solvent mixture such as acetic acid, under the influence of HBr or HCl, preferably at slightly elevated temperature. So the (R)-solketal ether of monobenzyl chloro-nitrocatechol is debenzylated under simultaneous cleavage of the isopropyl group of the solketal moiety to the corresponding bromohydrin acetate with 45% HBr (8 eq.) in acetic acid at 35° C.; 88% yield after 0.25 hour. The corresponding (S)-solketal ether is deprotected in 1.5 hour (yield 78%).

The subsequent ring-closure reaction of the compound obtained in this manner is carried out under alkaline conditions. So the desired (R)-7-chloro-2,3-dihydro-5-nitro-benzodioxin-2-methanol is obtained by a ring-closure in ethanol with 2N NaOH (16 eq.) in 1 hour at room temp.; ee=96%. Yield, including deprotection, 60%.

The corresponding (S)-stereoisomer is obtained in a yield of 90% (ee=92%) by reaction with 7 eq. 2N NaOH in ethanol at 23° C. after 2 hours.

The solketal ethers, prepared according to Example IX, are successively subjected to a solketal cleavage, preferably with HCl or HBr in acetic acid to the corresponding haloacetate, and to a ring-closure reaction as described above. Overall yields up to 80%. Stereoselectivity: ee=89%.

In the same manner the dialkylsolketal ethers of Example IX are ring-closed, yielding the desired 7-chloro-2,3-dihydro-5-nitro-benzodioxin-2-methanol enantiomer in overall yields of approx. 55%; ee=98%.

(c) The TCA-MIP ether obtained as described in Example VI(c) is subjected to the same deprotection-ringclosure reactions as described above: 45% HBr/AcOH and 2N NaOH (ethanol) successively. The chiral subst. benzodioxan-methanol is obtained in an overall yield of 90%, having an ee of >85%.

We claim:

1. A method for the stereoselective preparation of a hetero-bicyclic alcohol enantiomer, characterized in that a substantially pure enantiomer of the general formula

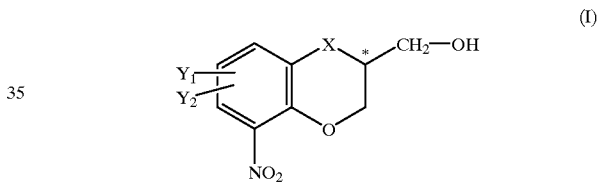

(I)

wherein X is O, S, NH or N-(C$_1$–C$_4$) alkyl,

Y$_1$ and Y$_2$ are each independently hydrogen or substituents selected from halogen, (C$_1$–C$_4$) alkyl, (C$_1$–C$_4$) alkoxy, (C$_1$–C$_4$)-haloalkyl, formyl, nitro and cyano;

the C*-atom has either the R or the S configuration;

is prepared from a compound of the general formula

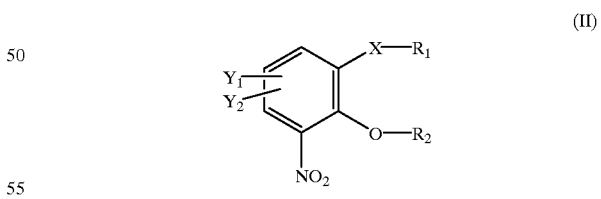

(II)

wherein:

X, Y$_1$ and Y$_2$ have the same meanings as defined above;

R$_1$ is hydrogen or a suitable protective group;

R$_2$ is hydrogen;

or wherein R$_1$ and R$_2$ together form an optionally mono- or di-(C$_1$–C$_3$) alkyl substituted methylene bridge;

by the following successive reaction steps:

(i) reaction with a substantially enantiomerically pure compound of the general formula

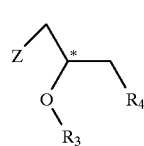
(III)

wherein:

Z is a hydroxy group or a suitable leaving group;

$R_3$ is a hydroxy-protective group;

$R_4$ is a halogen atom;

or wherein $R_3$ and $R_4$ together constitute a valence bond or a biradical of the formula $—C(R_{11})_2—O—$, wherein $R_{11}$ is a straight or branched ($C_1$–$C_4$) alkyl group;

the C*-atom has either the R or the S configuration;

after which reaction a substantially enantiomerically pure compound is formed of the general formula

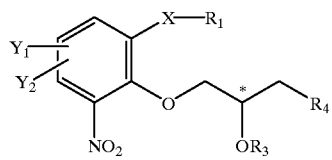
(IV)

wherein

X, $Y_1$, $Y_2$, $R_3$ and $R_4$ have the above meanings; and $R_1$ is hydrogen or a protective group;

(ii) subjection of the compound formed to a deprotection/ ring-closure reaction in (a) one single step, or (b) in a combined deprotection/activation step followed by a ringclosure step;

(iii) optionally deprotection of the hydroxy group of the ring-closed product.

2. A method as claimed in claim 1, characterized in that a substantially pure enantiomer of the general formula I as defined in claim 1, wherein X is O, is prepared by reaction of a catechol derivative of the general formula

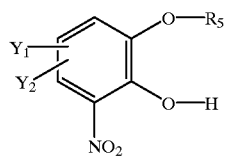
(V)

wherein:

$Y_1$ and $Y_2$ have the meanings given in claim 1; and $R_5$ is a suitable hydroxy-protective group;

with a substantially enantiomerically pure compound of the general formula

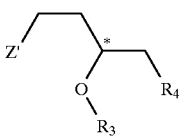
(VI)

wherein:

$R_3$ and $R_4$ have the above meanings; and

Z' is a halo or a sulphonate leaving group, preferably selected from tosyloxy, nosyloxy and mesyloxy;

after which reaction the substantially enantiomerically pure intermediate obtained, having the general formula

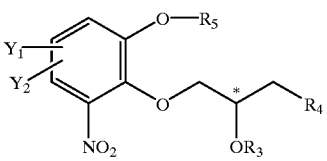
(VII)

is subjected to the successive reaction steps (ii) and (iii) as defined in claim 1.

3. A method as claims in claim 1, characterized in that a substantially pure enantiomer of the general formula I as defined in claim 1, wherein X is O, is prepared by reaction of a catechol derivative of the general formula

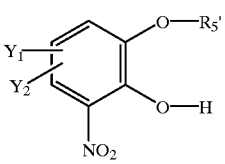
(Va)

wherein:

$Y_1$ and $Y_2$ have the meanings given in claim 1; and $R_5'$ is a hydroxy-protective group selected from the group consisting of ($C_1$–$C_8$) alkylcarbonyl and arylcarbonyl, wherein the aryl group is optionally substituted with one or more substituents selected from the group consisting of ($C_1$–$C_4$) alkoxy and halogen;

with a substantially enantiomerically pure compound of the general formula

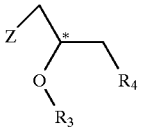
(IV)

wherein:

$R_3$ and $R_4$ have the above meanings; and

Z' is a halo or a sulphonate leaving group, preferably selected from toxyloxy, nosyloxy and mesyloxy;

after which reaction the substantially enantiomerically pure intermediate obtained, having the general formula

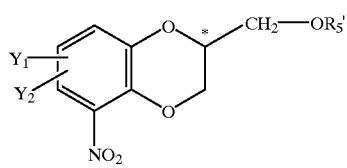
(VIIa)

is subjected to deprotection of the hydroxy group of the ring-closed product.

4. A method as claimed in claim 1, characterized in that a substantially pure enantiomer of the general formula I as defined in claim 1, wherein X is NH or N-($C_1$–$C_4$) alkyl, is prepared by reaction of a compound of the general formula

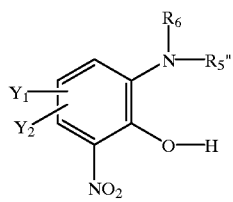
(VIII)

wherein:

$Y_1$ and $Y_2$ have the meanings given in claim 1; and
$R_5''$ is a suitable amino-protective group;
$R_6$ is hydrogen or ($C_1$–$C_4$) alkyl;

with a substantially enantiomerically pure compound of the general formula

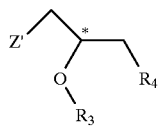
(IX)

wherein:

$R_3$ and $R_4$ have the above meanings; and
Z' is a halo or a sulphonate leaving group; preferably selected from tosyloxy, nosyloxy and mesyloxy;

after which reaction the substantially enantiomerically pure intermediate formed, having the general formula

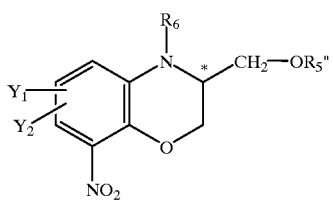
(X)

is subjected to the deprotection of the hydroxy group of the ring-closed product.

5. A method as claimed in claim 1, characterized in that a substantially pure enantiomer of the general formula I as defined in claim 1, wherein X is O, is prepared by reaction of a benzodioxole compound of the general formula

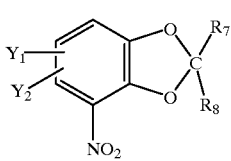
(XI)

wherein:

$Y_1$ and $Y_2$ have the meanings given in claim 1; and
$R_7$ and $R_8$ are each independently hydrogen or methyl;

with a chiral building block of the formula

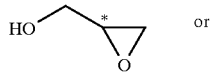
(XIIa)

or

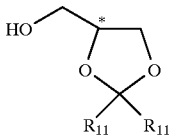
(XIIb)

wherein:

$R_{11}$ is a straight or branched ($C_1$–$C_4$)alkyl group;
the C*-atom has either the R or the S configuration;

after which reaction the substantially enantiomerically pure intermediate obtained, having the general formula

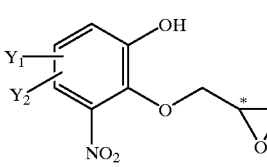
(XIIIa)

or

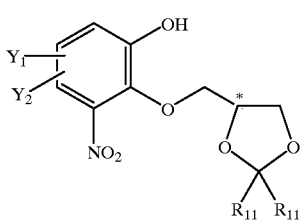
(XIIIb)

is subjected to the reaction step ii) as defined in claim 1.

6. A method as claimed in claim 1, characterized in that the ring-closure step in reaction (ii) is carried out in an apolar organic solvent with the aid of a phase transfer catalyst.

7. An enantiomerically pure compound to be used as an intermediate in the method of claim 1, having the general formula

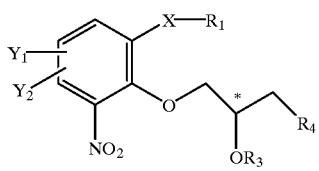
(IV)

wherein:

Y$_1$, Y$_2$, X, R$_3$ and R$_4$ have the meanings given in claim 1, and

R$_1$ has the meaning given in claim 1;

the C*-atom has either the R or the S configuration.

8. A method of preparing a catechol derivative, to be used in the method of claim 2 and having the general formula

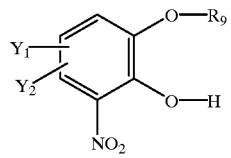
(XIV)

wherein:

Y$_1$ and Y$_2$ have the meanings given in claim 1, and

R$_9$ is an optionally substituted benzoyl group, a (C$_1$–C$_4$) alkylcarbonyl group or a tri(C$_1$–C$_4$)alkylsilyl group;

by reaction of a substituted catechol of the general formula

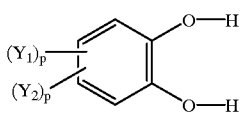
(XV)

wherein:

Y$_1$ and Y$_2$ have the above meanings, and p and q are 0 or 1;

with a compound of the general formula (R$_9$')$_2$O or R$_9$'Hal or (R$_{14}$)$_3$SiHal wherein:

R$_9$' is an optionally substituted benzoyl group or a (C$_1$–C$_6$)alkylcarbonyl group;

R$_{14}$ is (C$_1$–C$_4$)alkyl; and

Hal is halogen;

in the presence of an organic base, preferably a tert. amine or a mixture of organic bases, in a catalytic amount;

characterized in that the reaction is carried out in an apolar organic solvent or without a solvent, after which the compound obtained, having the general formula

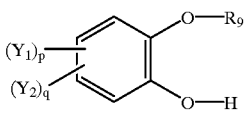
(XVIa)

is successively subjected to an aromatic substitution reaction to introduce substituents Y$_1$ and Y$_2$ into the aromatic nucleus, if necessary, and to a nitration.

9. A compound to be used as an intermediate in the method of claim 5, having the general formula

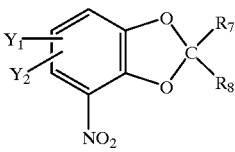
(XI)

wherein:

Y$_1$ and Y$_2$ have the meanings given in claim 1, with the proviso that Y$_1$ or Y$_2$ may not be a 7-alkoxy group; and R$_7$ and R$_8$ are each independently hydrogen or methyl.

10. A process for the preparation of the compound with the general formula XI as defined in claim 9, characterized in that a catechol compound with the general formula XV as defined in claim 8 is converted by the following reaction steps, (i) selective protection of one of the free hydroxy groups;

(ii) optional introduction of one or both of the substituents Y$_1$ and Y$_2$;

(iii) selective nitration of the position ortho to the unsubstituted hydroxy group;

(i) deprotection of the protected hydroxy group;

(v) formation of the benzodioxole moiety by reaction with a compound of the general formula

(XVII)

wherein:

R$_7$ and R$_8$ have the meanings given in claim 12;

R$_9$ and R$_{10}$ are each individually chlorine, bromine or (C$_1$–C$_4$)alkoxy or form together an oxygen atom.

11. A method as claimed in claim 2, characterized in that the ring-closure step in reaction (ii) is carried out in an apolar organic solvent with the aid of a phase transfer catalyst.

12. A method as claimed in claim 4, characterized in that the ring-closure reaction is carried out in an apolar organic solvent with the aid of a phase transfer catalyst.

13. A method as claimed in claim 5, characterized in that the ring-closure reaction is carried out in an apolar organic solvent with the aid of a phase transfer catalyst.

14. A method of preparing a substantially enantiomerically pure compound of the general formula

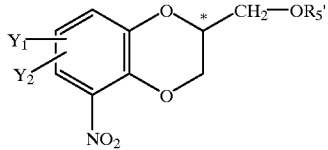
(VIIa)

wherein:

$Y_1$ and $Y_2$ are each independently hydrogen or substituents selected from halogen, $(C_1-C_4)$ alkyl, $(C_1-C_4)$ alkoxy, $(C_1-C_4)$-haloalkyl, formyl, nitro and cyano;

$R_5'$ has the meaning given in claim 3;

the C*-atom has either the R or the S configuration, characterized in that a compound of the general formula

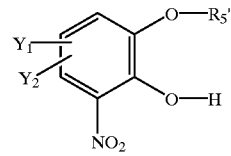
(Va)

wherein the symbols having the meanings given in claim 3; is reacted with a substantially enantiomerically pure compound of the general formula

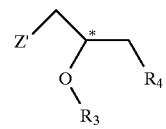
(VI)

wherein the symbols also have the meanings given in claim 3.

* * * * *